United States Patent [19]

Blumbach et al.

[11] Patent Number: 4,470,983
[45] Date of Patent: Sep. 11, 1984

[54] CEPHALOSPORIN DERIVATIVES

[75] Inventors: Jürgen Blumbach, Frankfurt am Main; Walter Dürckheimer, Hattersheim am Main; Karl Seeger, Hofheim am Taunus, all of Fed. Rep. of Germany

[73] Assignee: Hoechst Aktiengesellschaft, Frankfurt am Main, Fed. Rep. of Germany

[21] Appl. No.: 236,554

[22] Filed: Feb. 20, 1981

[30] Foreign Application Priority Data

Feb. 23, 1980 [DE] Fed. Rep. of Germany ....... 3006888

[51] Int. Cl.³ ................. C07D 501/36; A61K 31/545
[52] U.S. Cl. ..................... 424/246; 544/27; 544/16; 544/22; 544/21
[58] Field of Search ............ 544/27; 424/246; 544/28, 30, 22, 16, 21, 22

[56] References Cited

U.S. PATENT DOCUMENTS

| | | | |
|---|---|---|---|
| 4,098,888 | 7/1978 | Ochiai et al. | 544/25 |
| 4,217,348 | 8/1980 | Treuner et al. | 424/246 |
| 4,226,866 | 10/1980 | Christensen et al. | 424/248.51 |
| 4,252,802 | 2/1981 | Denzel et al. | 424/246 |
| 4,278,671 | 7/1981 | Ochiai et al. | 544/27 |
| 4,283,397 | 8/1981 | Hannah | 424/246 |
| 4,303,655 | 12/1981 | Kamiya et al. | 424/246 |

FOREIGN PATENT DOCUMENTS 2765 7/1979 European Pat. Off. .
34760 9/1981 European Pat. Off. .
2294690 7/1976 France .
2034692 6/1980 United Kingdom .

OTHER PUBLICATIONS

"Protective Groups in Organic Chemistry", J. F. W. McOmie, Plenum Press, New York, 1973, pp. xi, 183.
Ochiai et al., J. Antibiotics 34, 171–177 (1981).

Primary Examiner—Nicholas S. Rizzo
Attorney, Agent, or Firm—Curtis, Morris & Safford

[57] ABSTRACT

What are disclosed are cephalosporin compounds of the formula

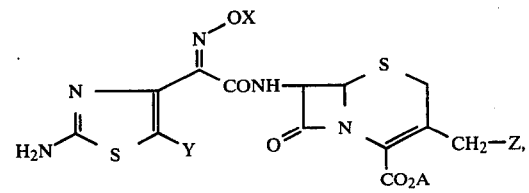

pharmaceutical preparations which are active against bacterial infections and in which these cephem compounds are present, process for the preparation of the cephem compounds and of the pharmaceutical preparations, use of the cephem compounds for combating bacterial infections, and compounds used as starting materials in the synthesis of said cephem compounds.

4 Claims, No Drawings

CEPHALOSPORIN DERIVATIVES

The invention relates to cephalosporin derivatives of the general formula I

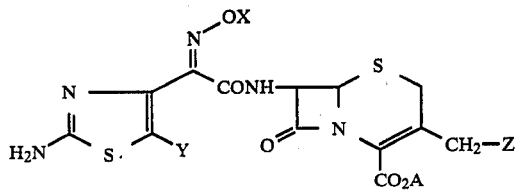

in which X represents hydrogen, optionally substituted alkyl having 1 to 4 C atoms, optionally substituted carboxymethyl which can also be present in the form of its physiologically acceptable salts, optionally substituted alkoxycarbonylmethyl having 1 to 4 C atoms in the alkyl part, optionally substituted aminocarbonylmethyl or optionally substituted cyanomethyl, Y represents halogen, Z represents azide, optionally substituted pyridinium or S-Het, Het denoting an optionally substituted five- or six-membered heterocyclic ring containing at least one nitrogen atom, and A represents hydrogen, an ester radical which can easily be cleaved or a physiologically acceptable cation.

If X represents alkyl having 1 to 4 C atoms, there may be mentioned in particular the radicals methyl, ethyl, propyl, iso-propyl, butyl and iso-butyl, which can also be substituted, for example by halogen, in particular bromine or chlorine, by hydroxyl or by amino which can also be monosubstituted or disubstituted, for example by alkyl having 1 to 4 C atoms, preferably methyl.

If X represents alkoxycarbonylmethyl having 1 to 4 C atoms in the alkyl part, methoxycarbonylmethyl and ethoxycarbonylmethyl are particularly suitable.

X in the above meaning of carboxymethyl, which can also be present in the form of its physiologically acceptable salts, alkoxycarbonylmethyl, aminocarbonylmethyl and cyanomethyl can be monosubstituted or disubstituted in the methylene group, for example by alkyl having 1 to 4 C atoms, preferably methyl, it also being possible in particular for two alkyl substituents to be joined together to form a 3- to 6-membered carbocyclic ring.

Preferred radicals X which may be specifically mentioned are hydrogen, ethyl, n-propyl, iso-propyl, n-butyl, iso-butyl, carboxymethyl, methoxycarbonylmethyl, ethoxycarbonylmethyl, aminocarbonylmethyl and cyanomethyl. Methyl is particularly preferred.

Preferred meanings for Y are bromine and chlorine; however, chlorine is particularly preferred.

Z can represent azide, pyridinium, optionally substituted pyridinium, preferably 4-aminocarbonyl-pyridinium, or also S-Het, Het representing a 5-membered heterocyclic ring which is optionally also totally or partially hydrogenated and which can also contain further hetero-atoms, such as nitrogen, sulfur or oxygen, in addition to a nitrogen atom, such as, for example, thiazole, thiadiazole, triazole, oxadiazole or tetrazole, or represents a 6-membered heterocyclic ring having 1-3 nitrogen atoms, which is optionally also totally or partially hydrogenated, such as, for example, pyridine, pyrimidine or triazine, in particular 1,2,4-triazin-3-yl, which can optionally be monosubstituted or disubstituted by alkyl groups having 1-4 C atoms, preferably methyl and ethyl, trifluoromethyl, carboxyl, carboxymethyl, alkoxycarbonylmethyl having 1-4 C atoms in the alkyl part, preferably methoxy- or ethoxy-carbonylmethyl, hydroxyl, hydroxymethyl, oxo, amino, alkyl- and dialkyl-amino having 1-4 C atoms in the alkyl part, preferably methyl- or ethyl-amino, or acylamino having 1-4 C atoms in the acyl part, preferably formyl or acetyl, or by 5- or 6-membered heteroaryl, in particular thienyl and pyridyl.

Particularly preferred meanings of Het which may be mentioned are 1,3,4-thiadiazol-2-yl, 2-methyl-1,3,4-thiadiazol-5-yl, 2-ethyl-1,3,4-thiadiazol-5-yl, 2-trifluoromethyl-1,3,4-thiadiazol-5-yl, 2-hydroxymethyl-1,3,4-thiadiazol-5-yl, 2-amino-1,3,4-thiadiazol-5-yl, 2-methyl-1,3,4-oxadiazol-5-yl, 2-hydroxymethyl-1,3,4-oxadiazol-5-yl, 1,3,4-triazol-2-yl, 1-methyl-1,3,4-triazol-2-yl, 1,2-dimethyl-1,3,4-triazol-5-yl, 1,2,3-triazol-4-yl, 2-thien-2-yl-1,3,4-triazol-5-yl, 3-methyl-1,2,4-thiadiazol-5-yl, 5-carboxymethyl-4-methyl-thiazol-2-yl, tetrazol-5-yl, 1-methyl-tetrazol-5-yl, 1-oxido-pyridin-2-yl, 3,6-diamino-pyrimidin-2-yl, 6-hydroxy-4-methyl-4,5-dihydro-5-oxo-1,2,4-triazin-3-yl and 6-hydroxy-2-methyl-2,5-dihydro-5-oxo-1,2,4-triazin-3-yl.

In the meaning of A, the tert.-butyl ester and trimethylsilyl ester, and also the benzyl, benzhydryl, trichloroethyl, p-methoxybenzyl or p-nitrobenzyl ester, may be mentioned as preferred esters which can easily be cleaved, these esters having the character of a chemical protective group.

Examples of physiologically acceptable cations A which may be mentioned are an alkali metal ion, in particular the sodium and potassium ion, an alkaline earth metal ion, in particular the calcium and magnesium ion, and the ammonium ion, but preferably a sodium ion, and also an optionally substituted alkylated ammonium ion, it being possible for an alkyl radical to have 1-4 C atoms, such as, preferably, triethylammonium, diethylammonium and dimethylammonium, or morpholinium, benzylammonium, procainium, L-argininium and L-lysinium. Corresponding physiologically acceptable cations are also possible in the case where X is present in the form of a salt of the carboxymethyl group.

The XO group in the compounds of the general formulas I, III, IV and V can be present either in the syn form or in the anti form. The syn form is particularly preferred according to the invention. The notation syn or anti expresses the spatial arrangement relative to the carboxamido group in the compounds I and IV, to the carboxyl group in the compounds III and to the alkoxycarbonyl group in the compounds V, the syn position being the one in which the XO group is located on the same side of the C=N double bond as the carboxamido, carboxyl or alkoxycarbonyl group.

2-Aminothiazoles of the general formulae I, III, IV and V can in each case occur in two tautomeric forms, which are present in equilibrium with one another and can be represented by the following equilibrium equations:

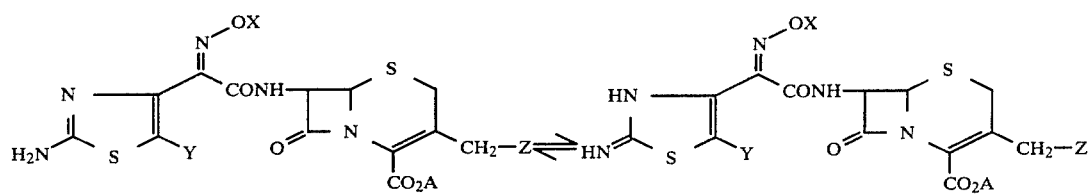

I

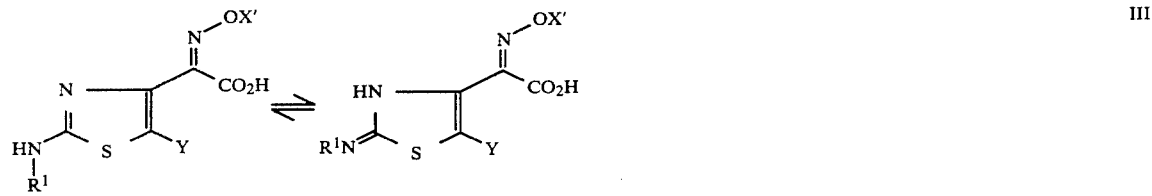

III

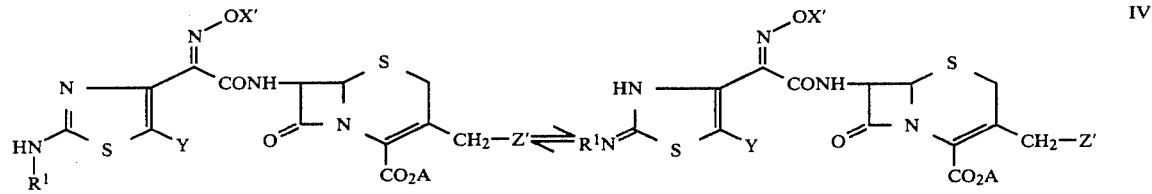

IV

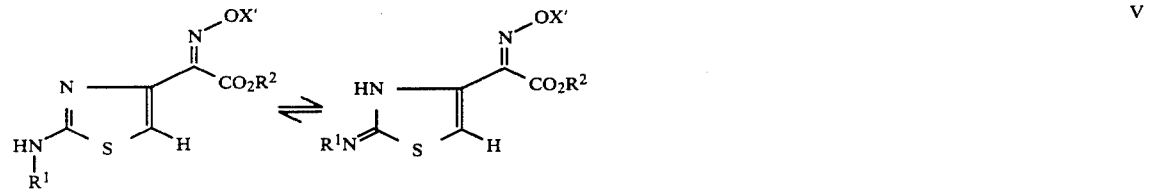

V

In the present notes, the two tautomers are not shown in every case when the formulae are given. For practical reasons, only the aminothiazole tautomer is shown

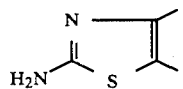

and the nomenclature of the compounds also relates to this.

The invention further relates to a process for the preparation of cephem compounds of the general formula I, which comprises reacting lactams of the general formula II

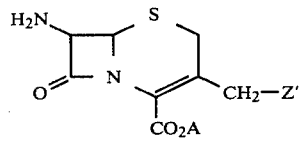

II in which A has the meaning given above and Z' represents Z, acyloxy having 1-4 C atoms in the acyl part or halogen, with a carboxylic acid of the general formula III

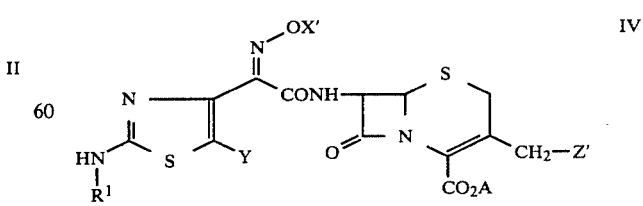

III or with an activated derivative thereof, in which formula Y has the abovementioned meaning, $R^1$ represents hydrogen or an amino protective group known from peptide chemistry and X' represents X, a group which can easily be cleaved or a group

—CH$_2$CO$_2$R$^3$ in which $R^3$ denotes a radical which can be cleaved under mild conditions, to give a compound of the general formula IV

IV in which $R^1$, X', Y, Z' and A have the abovementioned meanings, cleaving the radical $R^1$ when it denotes a protective group, converting the radical X' to X, in the case where it does not denote X, and converting the radical Z' to Z, in the case where it does not denote Z, the order in which the cleavage of $R^1$ and the conversion of X' and Z' to X and Z take place being interchangeable as desired.

In the formulas II, III and IV, $R^1$ represents hydrogen or an amino protective group known from peptide chemistry, such as, for example, optionally substituted alkyl, such as, preferably, tert.-butyl, tert.-amyl, benzyl, p-methoxybenzyl, benzhydryl, trityl and phenylethyl, optionally substituted aliphatic acyl, such as, for example, formyl, chloroacetyl, bromoacetyl, trichloroacetyl and trifluoroacetyl, or optionally substituted alkoxycarbonyl, such as, for example, trichloroethoxycarbonyl or benzyloxycarbonyl, X' represents X, a group which can easily be cleaved, such as, for example, formyl, trifluoroacetyl, chloroacetyl, bromoacetyl, trityl, tert.-amyl, tert.-butyl, benzhydryl and tetrahydropyranyl, but preferably tert.-butyl, trityl and tetrahydropyranyl, or also a group of the formula $-CH_2CO_2R^3$, in which $R^3$ denotes a radical which can be cleaved under mild conditions, such as, preferably, trichloroethyl, tert.-butyl, benzyl, p-methoxyphenyl, benzhydryl or trityl, and Z' represents Z, acyloxy having 1–4 C atoms in the acyl part, preferably formyloxy and acetoxy, or halogen, such as, preferably, chlorine and bromine.

Particularly suitable activated derivatives of the carboxylic acids of the general formula III are the halides, preferably chlorides and bromides, and also the anhydrides and mixed anhydrides, the azides and the activated esters, preferably those with p-nitrophenol, 2,4-dinitrophenol, methylenecyanohydrin, N-hydroxysuccinimide and N-hydroxyphthalimide and particularly preferably those with 1-hydroxybenzotriazole and 6-chloro-1-H-hydroxybenzotriazole. Particularly suitable mixed anhydrides are those with lower alkanoic acids, for example with acetic acid and particularly preferably with substituted acetic acids, such as, for example, trichloroacetic acid, pivalic acid or cyanoacetic acid. However, mixed anhydrides which are also particularly suitable are those with carbonic acid half-esters, which are obtained, for example, by reacting the carboxylic acids III in which $R^1$ does not denote hydrogen with benzyl, p-nitrobenzyl, isobutyl, ethyl or allyl chloroformate.

The activation can also be carried out by reacting the carboxylic acid of the formula III with a product resulting from the reaction of, for example, phosgene, thionyl chloride, thionyl bromide, oxalyl chloride, phosphorus pentachloride or phosphorus oxychloride with an N-dialkyl-substituted carboxamide, such as, for example, dimethylformamide, dimethylacetamide or N-methylpyrrolidone. The product resulting from the reaction of dimethylformamide and one of the above-mentioned halides is also designated in the literature as a Vilsmeier reagent.

The activated derivatives can be reacted as isolated substances, but they can also be reacted in situ. The reaction of the cephem derivatives II with the carboxylic acid III, or with an activated derivative thereof, is generally carried out in the presence of an inert solvent. Particularly suitable inert solvents are chlorinated hydrocarbons, such as, preferably, methylene chloride and chloroform; ethers, such as, for example, diethyl ether, diisopropyl ether and, preferably, tetrahydrofuran and dioxane, ketones, such as, preferably, acetone and butanone, amides, such as, preferably, dimethylformamide, dimethylacetamide and N-methylpyrrolidone, or water. It can also prove advantageous to use mixtures of the said solvents. This is frequently the case when the cephem compound II is reacted with an activated derivative of the carboxylic acid III which has been produced in situ.

The reaction of cephem compounds II with carboxylic acids III, or their activated derivatives, can take place in a temperature range of about $-50°$ to about $+80°$ C., preferably between $-20°$ and $+50°$ C., but particularly preferably between $-20°$ C. and room temperature.

The reaction time depends on the reactants, the temperature and the solvent or the solvent mixture, and is normally between about ¼ and about 72 hours.

In specific cases, it can also prove advantageous to react the free carboxylic acid of the formula III directly with a cephem compound of the formula II in which A denotes an ester radical which can easily be cleaved, such as, preferably, tert.-butyl or trimethylsilyl, a water-binding agent advantageously being added in an approximately equimolar amount. Examples of possible water-binding agents are carbodiimides, in particular dicyclohexylcarbodiimides. This reaction is carried out in inert solvents, such as, preferably, methylene chloride, dimethylformamide, tetrahydrofuran, dioxane or also mixtures.

The reaction of activated derivatives of the carboxylic acids of the formula III with cephem compounds of the formula II is preferably carried out in an alkaline medium at a pH of more than 7. For this purpose, a base is added to the reaction mixture, such as, preferably, potassium carbonate or sodium carbonate, potassium bicarbonate or sodium bicarbonate, potassium hydroxide or sodium hydroxide, pyridine or a trialkylamine, such as, for example, triethylamine, N-methylmorpholine, ethyldiisopropylamine or potassium tert.-butylate.

Preferably, the reaction can also be carried out in such a way that a 1-hydroxybenzotriazole ester or a 6-chlorohydroxybenzotriazole ester of the carboxylic acids of the general formula III is reacted directly with cephem compounds of the formula II, in a solvent, without the addition of an acid-binding agent. Open-chain and cyclic tertiary amides have proved to be particularly good solvents, dimethylformamide, dimethylacetamide and N-methylpyrrolidone being particularly preferred.

If cephem compounds of the formula IV still contain a radical $R^1$, X' and/or Z', the compounds of the formula I can be obtained therefrom by cleaving the radical $R^1$, in the case where it does not denote hydrogen, converting X' to X, in the case where it does not denote X, and converting Z' to Z, in the case where it does not represent Z. The order in which the cleavage of $R^1$ and the conversions of X' and Z' to X and Z take place can be interchanged as desired, but, as a rule, the conversions of $R^1$ to hydrogen and X' to X are carried out first and the conversion of Z' to Z is not carried out until afterwards.

In compounds of the formula IV, the conversion of the radical Z' to Z, in the case where it does not denote Z, can take place by reaction with a compound containing the nucleophilic radical Z. In this case, Z' can represent acyloxy having 1 to 4 C atoms, but in particular formyloxy and acetoxy, and halogen, preferably chlorine or bromine. Compounds containing a nucleophilic radical Z which may be mentioned in particular are hydrazoic acid, optionally substituted pyridine derivatives, such as, in particular, pyridine and 4-aminocarbonylpyridine, and compounds of the formula HS-Het, Het having the abovementioned meanings.

The reaction is preferably carried out in such a way that one equivalent of a compound of the general formula IV is reacted with at least one equivalent of a compound containing a nucleophilic radical Z, in particular the compounds mentioned above as preferred, in a solvent which does not hinder the reaction.

An up to 10-fold excess of the nucleophilic compound has an advantageous effect on the yield. The excess is preferably 0–200%.

Examples of solvents which do not hinder the reaction are water, acetone, butanone, chloroform, nitrobenzene, methylene chloride, ethylene chloride, dimethylformamide, dimethylacetamide, N-methylpyrrolidone, methanol, ethanol, ethyl acetate, butyl acetate, diethyl ether, diisopropyl ether, tetrahydrofuran and acetonitrile.

Of the solvents, the hydrophilic solvents, preferably acetone, methanol, ethanol, dimethylformamide and acetonitrile, can also be used in a mixture with water.

The reaction is carried out in a pH range of 5 to 8 and preferably at neutral pH.

If the compounds containing the nucleophilic radical Z, in particular hydrazoic acid and the compounds of the formula HS-Het, are used in the free form, the reaction is preferably carried out in the presence of a base. An example of a suitable base is an inorganic base, such as an alkali metal hydroxide, alkali metal carbonate or alkali metal bicarbonate.

An organic base, such as, for example, a trialkylamine or a quaternary ammonium base, can also be used.

However, the compounds containing the nucleophilic radical can also be used in the form of their salts, preferably their sodium or potassium salts.

The reaction temperature can be varied in a wide range. As a rule, the reaction is carried out at room temperature or while heating to the reflux temperature of the solvents or solvent mixtures used. However, it is advantageous not to exceed 80° C.

The cleavage of $R^1$ can be carried out by mild methods which are generally customary in β-lactam and peptide chemistry, such as hydrolysis in acids, preferably formic acid or trifluoroacetic acid, or also hydrogenolysis in the presence of noble metal catalysts. However, depending on the protective group, it is also possible to use special cleavage reagents, such as, for example, optionally substituted thioureas for the removal of α-halogenoacyl groups.

The conversion of the group X' to X, in the case where it does not denote X, can also be carried out by mild hydrolytic or hydrogenolytic methods which are customary in β-lactam and peptide chemistry, and hydrolyses in inorganic and organic acids, such as, preferably, trifluoroacetic acid or dilute formic acid, should be mentioned in particular.

Esters of the formulas I and IV in which A denotes a radical which can easily be cleaved, and which are obtained in the reaction according to the invention, can, if desired, be converted to compounds of the formula I or IV in which A denotes hydrogen or a physiologically acceptable cation, as has been described above, by a mild method known from the literature, for example hydrolytically or hydrogenolytically. Analogously, it is also possible to cleave the group $R^3$ from the radical X' when the latter denotes $—CH_2CO_2R^3$.

The carboxylic acids III used for the acylation can be prepared by various processes.

Thus, for example, compounds of the formula III in which Y denotes halogen are obtained by reacting compounds of the formula V

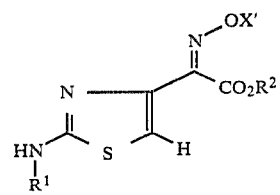

in which $R^1$ and X' have the abovementioned meanings and $R^2$ denotes an alkyl radical having 1–4 C atoms or an aralkyl radical, such as, preferably, benzylethyl or phenylethyl, with a halogenating reagent, and optionally converting the radical $R^1$ and/or the radical X' to the form which is favorable for the following reactions, for example by introducing or cleaving a protective group, and/or converting the ester V thus obtained to the carboxylic acid of the general formula III, in a manner which is in itself known.

Suitable halogenating agents which can be used are the elementary halogens, such as, preferably, bromine and chlorine, trihalogenoisocyanuric acids, such as, preferably, trichloroisocyanuric acid, N-halogenoamides, such as, preferably, chloramine-T, N-chloroacetamide and N-bromoacetamide, N-halogenoimides, such as, preferably, N-chlorosuccinimide, N-bromosuccinimide, N-chlorophthalimide and N-bromophthalimide, or alkyl hypochlorites, such as, for example, tert.-butyl hypochlorite. As a rule, the reaction is carried out in a solvent which does not have an adverse influence on the reaction or which even allows it to proceed in the desired direction. Thus, in the case of alkyl hypochlorites, N-halogenoamides and N-halogenoimides, a polar solvent containing hydroxyl groups, which promotes the formation of positive halogen ions is recommended, such as, for example, formic acid, glacial acetic acid, water or alkanols, such as, for example, methanol, ethanol or isopropanol. In addition, but above all when using elementary halogen, it is also possible to recommend solvents such as chloroform, methylene chloride, tetrahydrofuran, dioxane or dimethylformamide, or mixtures thereof with one another or with the abovementioned solvents containing hydroxyl groups.

The reaction temperature is not critical, but it is preferably in the range between about $-20°$ C. and room temperature.

Compounds of the formula III in which Y denotes halogen can also be prepared by reacting thiourea with oximes of the formula

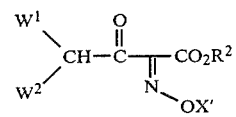

in which $W^1$ and $W^2$ can be identical or different and represent bromine or chlorine, and X' and $R^2$ have the abovementioned meanings, if appropriate by subsequently introducing $R^1$ when it denotes an amino protective group known from peptide chemistry, as defined above, and/or by saponifying the ester of the formula V thus obtained to give the carboxylic acid of the general formula III.

The reaction is advantageously carried out with a stoichiometric amount of thiourea, in a solvent, such as ethanol or acetone, which contains water. The reaction should be carried out at room temperature and last a maximum of about 2 to 3 hours.

The starting compounds of the formula V are known from the literature or can be prepared by processes known from the literature.

If the radical $R^1$ in the general formulae III and V represents a group known from peptide chemistry as an amino protective group, which can easily be removed, its introduction into the amino group can be carried out by the method known from peptide chemistry for amino protective groups. For example, if $R^1$ represents the trityl group, its introduction can be carried out with triphenylchloromethane, the reaction advantageously being carried out in an organic solvent, such as, for example, halogenated hydrocarbons, in the presence of bases, such as, preferably, triethylamine.

If X' in the formulae III and V represents a group which can easily be cleaved, its introduction can take place in a method known from the literature, which is familiar to those skilled in the art of protecting hydroxyl groups.

Not only in the preparation of the starting materials III or V which contain a group

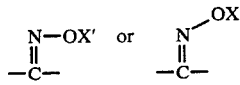

in the syn position, but also in the preparation of all intermediates and in the further reaction thereof to give IV and I, it is advantageous to apply the mildest possible reaction conditions, such as are known from the literature to those skilled in the art of carrying out reactions with syn compounds, such as, for example, no elevated temperatures, no extended reaction times, no substantial excesses of acid reactants, and so on, in order to avoid any possible flipping of the oxime group into the anti form.

The compounds of the formula I obtained according to the invention exhibit remarkably good antibacterial activities, both against Gram-positive and against Gram-negative bacterial germs.

The new compounds also have an unexpectedly good activity against penicillinase- and cephalosporinase-forming bacteria. Because they additionally exhibit favorable toxicological and pharmacological properties, they represent valuable chemotherapeutic agents.

The invention thus also relates to medicinal preparations for the treatment of microbial infections, which preparations contain one or more of the compounds according to the invention.

The products according to the invention can also be used in combination with other active ingredients, for example from the series of the penicillins, cephalosporins or aminoglycosides.

The compounds of the formula I can be administered orally, intramuscularly or intravenously.

Medicinal preparations which contain one or more compounds of the general formula I as the active ingredient can be prepared by mixing the compounds of the general formula I with one or more pharmacologically acceptable carriers or diluents, such as, for example, fillers, emulsifiers, lubricants, taste-correctors, dyestuffs or buffer substances, and converted to a suitable Galenical form of preparation, such as, for example, tablets, coated tablets, capsules or a solution or suspension suitable for parenteral administration. Examples of carriers or diluents which may be mentioned are tragacanth, lactose, agar-agar, polyglycols, talc, ethanol and water. For parenteral administration, suspensions or solutions in water are preferably used. It is also possible to administer the active ingredients as such, without carriers or diluents, in a suitable form, for example in capsules.

Suitable doses of the compounds of the general formula I are about 0.4 to 20 g/day and preferably 0.5 to 4 g/day for an adult of about 60 kg body weight. It is possible to administer single doses or, in general, multiple doses, it being possible for the single dose to contain the active ingredient in an amount of about 50 to 1,000 mg and preferably 100 to 500 mg.

The compounds I shown in the following table are examples of compounds which can be prepared, according to the invention, in addition to those mentioned in the illustrative embodiments:

| | | I |
|---|---|---|
| X | Y | Z |
| H | Cl | N——N (S, S, H) |
| H | Cl | N——N (S, S, CH₃) |
| H | Cl | N——N (S, S, CF₃) |
| H | Cl | N——N (S, S, NH₂) |
| H | Cl | N—C(CH₃)=N—S (thiazole) |
| H | Cl | N=C(CH₃)—S—CH₂CO₂H |
| H | Cl | N——N=N (S, N–CH₃) |

(Structure I: $H_2N-C(=N)-S-C(=N-OX)-CONH-\beta$-lactam-S-CH=C(CH_2-Z)-CO_2H with Y substituent)

-continued
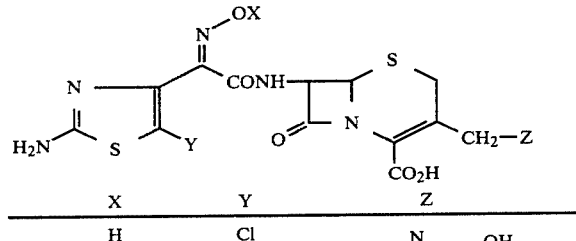
| X | Y | Z |
|---|---|---|
| H | Cl | 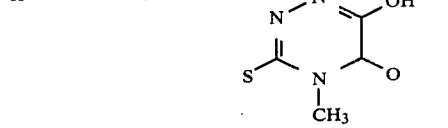 |
| H | Cl | 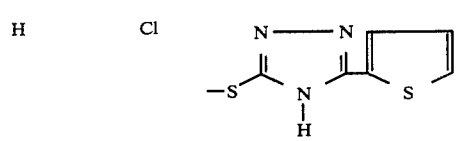 |
| CH₃ | Cl | 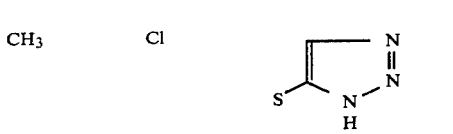 |
| CH₃ | Cl |  |
| CH₃ | Cl | 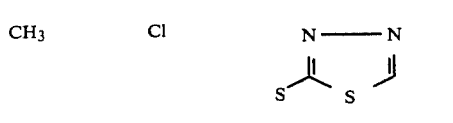 |
| CH₃ | Cl | 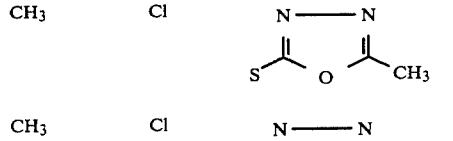 |
| CH₃ | Cl | 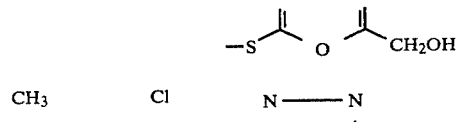 |
| CH₃ | Cl | 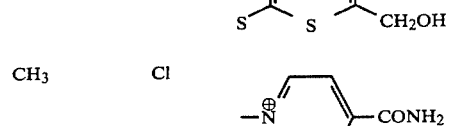 |
| CH₃ | Cl | 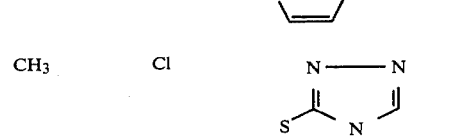 |
| CH₃ | Cl | 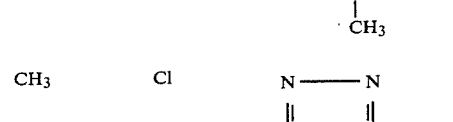 |
| CH₃ | Cl | 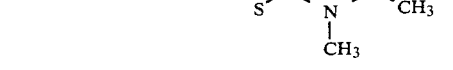 |
-continued
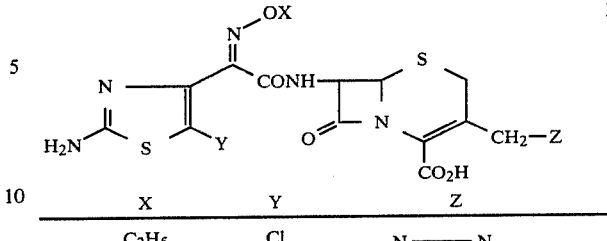
| X | Y | Z |
|---|---|---|
| C₂H₅ | Cl | 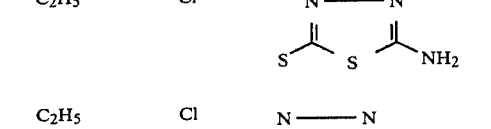 |
| C₂H₅ | Cl | 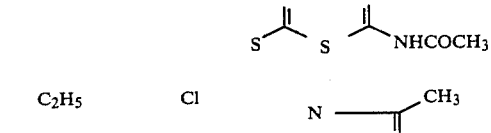 |
| C₂H₅ | Cl | 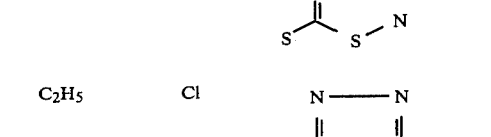 |
| C₂H₅ | Cl | 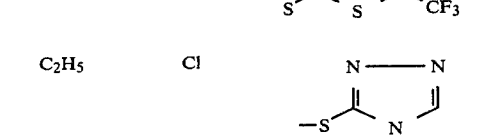 |
| C₂H₅ | Cl | 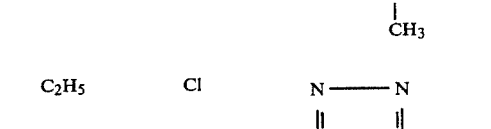 |
| C₂H₅ | Cl | 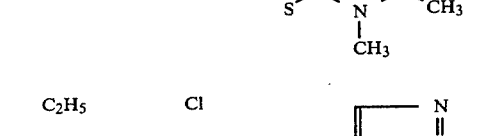 |
| C₂H₅ | Cl | 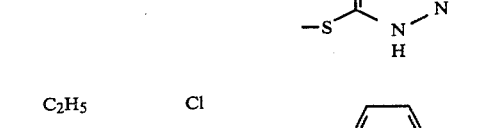 |
| C₂H₅ | Cl | 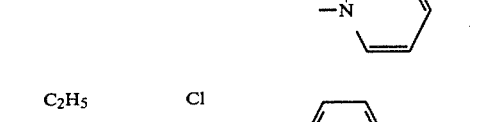 |
| C₂H₅ | Cl | 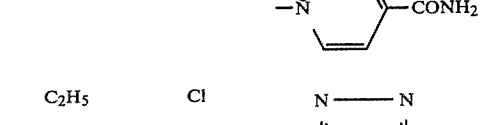 |
| C₂H₅ | Cl | 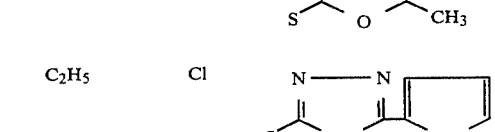 |

-continued

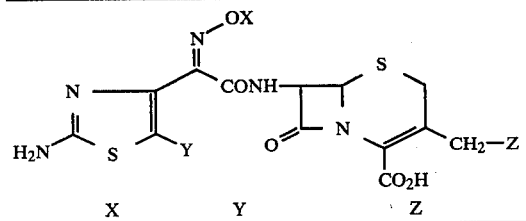

| X | Y | Z |
|---|---|---|
| $C_2H_5$ | Cl | 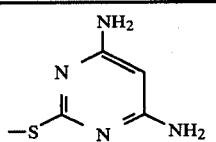 |
| $C_2H_5$ | Cl | 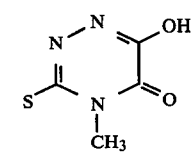 |
| $CH_2CO_2C_2H_5$ | Cl | $N_3$ |
| $CH_2CO_2C_2H_5$ | Cl | 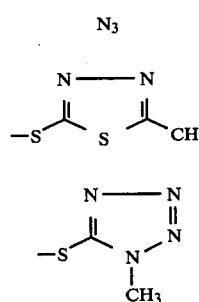 |
| $CH_2CO_2C_2H_5$ | Cl | 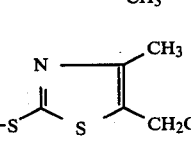 |
| $CH_2CO_2C_2H_5$ | Cl | 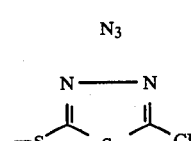 |
| $CH_2CO_2H$ | Cl | $N_3$ |
| $CH_2CO_2H$ | Cl | 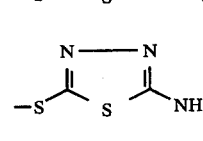 |
| $CH_2CO_2H$ | Cl | 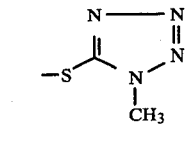 |
| $CH_2CO_2H$ | Cl | 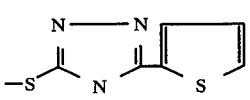 |
| $CH_2CO_2H$ | Cl | 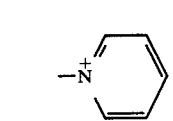 |
| $CH_3$ | Cl |  |

-continued

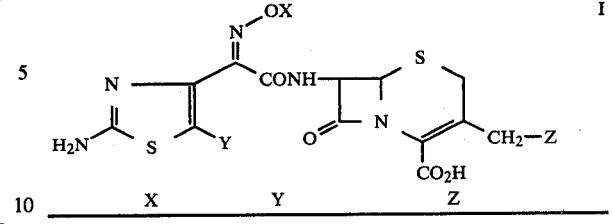

| X | Y | Z |
|---|---|---|
| $CH_2CO_2H$ | Cl | 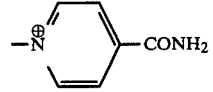 |
| $CH_2CO_2H$ | Cl | 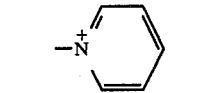 |
| $C(CH_3)_2CO_2H$ | Cl | 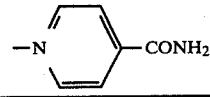 |
| $C(CH_3)_2CO_2H$ | Cl | |

The examples illustrate the invention without however restricting it.

The $R_f$ values indicated in the examples were determined by thin layer chromatography on 60 F 254 pre-coated silica gel plates from Messrs. Merck, Darmstadt.

EXAMPLE 1

7-[α-Syn-methoxyimino-α-(2-amino-5-chlorothiazol-4-yl)acetamido]-3-(1-methyltetrazol-5-yl-thiomethyl)-3-cephem-4-carboxylic acid 940 mg of α-syn-methoxyimino-α-(2-amino-5-chlorothiazol-4-yl)-acetic acid and 540 mg of 1-hydroxybenzotriazole were dissolved in 30 ml of tetrahydrofuran, and 824 mg of dicyclohexylcarbodiimide were added. After stirring for two hours at room temperature, the solid was filtered off. 1.35 g of 7-amino-3-(1-methyltetrazol-5-yl-thiomethyl)-3-cephem-4-carboxylic acid, which had been dissolved with 1.2 g of triethylamine in 30 ml of methylene chloride and then filtered through kieselguhr, were added to the mother liquor and the resulting mixture was stirred for 4 hours at room temperature. The reaction solution was filtered through kieselguhr and concentrated on a rotary evaporator. The residue was taken up in $H_2O$ at pH 6.0, the aqueous mixture was extracted three times with ethyl acetate, residual ethyl acetate was removed in vacuo and the aqueous phase was cooled to +5° and acidified to pH 1.6 with 2 N HCl. 1.2 g of the title compound could be isolated by filtration.

NMR (DMSO-$d_6$): δ=9.5 ppm (d, 1H, CON<u>H</u>); δ=7.3 ppm (s, 2H, N<u>H</u>$_2$); δ=5.75 ppm (q, 1H, C-7-H); δ=5.05 ppm (d, 1H, C-6-H); δ=4.3 ppm (broad, C<u>H</u>$_2$-S); δ=3.95 ppm [236 Hz] (s, 3H, tetrazole-CH$_3$); δ=3.85 ppm [231 Hz] (s, 3H, OCH$_3$, syn); δ=3.6 ppm (s, broad, C-2-C<u>H</u>$_2$).

EXAMPLE 2

7-[α-Syn-methoxyimino-α-(2-amino-5-chlorothiazol-4-yl)-acetamido]-3-(1-methyltetrazol-5-yl-thiomethyl)-3-cephem-4-carboxylic acid 4.9 g of 7-[α-syn-methoxyimino-α-(2-amino-5-chlorothiazol-4-yl)-acetamido]-cephalosporanic acid and 1.5 g of sodium 1-methyltetrazol-5-yl-thiolate were stirred for 3 hours in 100 ml of $H_2O$ at pH 6.5 to 7.0 and at 60°. After cooling, the mixture was adjusted to pH 4.5 with 2 N HCl and extracted twice with ethyl acetate and, after removal of residual ethyl acetate in vacuo at 5°, the aqueous phase was adjusted to pH 2.0 with 2 N HCl. After stirring for ¼ hour, the solid was filtered off and dried. This yielded 3.7 g of the title compound, the physical constants of which were identical to those of the compound prepared in Example 1.

EXAMPLE 3

7-[α-Syn-methoxyimino-α-(2-amino-5-chlorothiazol-4-yl)-acetamido]-3-azidomethyl-3-cephem-4-carboxylic acid 2.32 g of α-syn-methoxyimino-α-(2-amino-5-chlorothiazol-4-yl)-acetic acid were dissolved in 25 ml of tetrahydrofuran, 1.36 g of 1-hydroxybenzotriazole were added and the resulting mixture was warmed to 45°. After the addition of 2.16 g of dicyclohexylcarbodiimide, the mixture was stirred for 2 hours at room temperature and the urea which had precipitated out (2.18 g) was filtered off and washed with 15 ml of tetrahydrofuran.

The combined filtrates were brought together with a solution of 2.55 g of 7-amino-3-azidomethyl-3-cephem-4-carboxylic acid and 3.0 g of triethylamine in 40 ml of $CH_2Cl_2$ and the resulting mixture was stirred for 6 hours at room temperature. The crystals formed were filtered off and washed with a small amount of $CH_2Cl_2$. This yields 2.3 g of the triethylammonium salt of the title compound.

NMR (DMSO-$d_6$): δ=9.5 ppm (d, 1H, CONH); δ=7.4 ppm (broad, 2H, $NH_2$); δ=5.6 ppm (q, 1H, C-7-H); δ=5.1 ppm (d, 1H, C-6-H); δ=3.8 ppm [231 Hz] (s, 3H, $OCH_3$, syn); δ=4.3 ppm (broad, $CH_2$-S); δ=3.4 ppm (broad, C-2-$CH_2$); δ=3.0 ppm (q, 6H, N-$CH_2$); δ=1.2 ppm (t, 9H, $NCH_2CH_3$).

2.0 g of the triethylammonium salt of the title compound were dissolved in 50 ml of $H_2O$ at 0° and the resulting solution was adjusted to pH 2.1 with 2 N HCl. 1.36 g of the title compound could be isolated by filtration.

NMR (DMSO-$d_6$): δ=9.5 ppm (d, 1H, CONH); δ=7.3 ppm (broad, 2H, $NH_2$); δ=5.6 ppm (q, 1H, C-7-H); δ=5.05 ppm (d, 1H, C-6-H); δ=4.4 ppm (AB, $CH_2$-$N_3$); δ=3.8 ppm [232 Hz] (s, 3H, $OCH_3$, syn); δ=3.4 ppm (broad, C-2-$CH_2$).

EXAMPLE 4

7-[α-syn-methoxyimino-α-(2-amino-5-chlorothiazol-4-yl)-acetamido]-3-(2-methyl-1,3,4-thiadiazol-5-yl-thiomethyl)-3-cephem-4-carboxylic acid 1.18 g of α-syn-methoxyimino-α-(2-amino-5-chlorothiazol-4-yl)-acetic acid and 680 mg of 1-hydroxybenzotriazole were dissolved in 50 ml of tetrahydrofuran, and 1.03 g of dicyclohexylcarbodiimide were added. After stirring for two hours, the solid was filtered off. A suspension of 1.72 g of 7-amino-3-(2-methyl-1,3,4-thiadiazol-2-yl-thiomethyl)-3-cephem-4-carboxylic acid and 2.0 g of triethylamine in 50 ml of $CH_2Cl_2$ was added to the mother liquor.

The resulting mixture was stirred overnight at room temperature, the solvent was distilled off in vacuo, the residue was taken up in 60 ml of $H_2O$ and the aqueous mixture was extracted four times with ethyl acetate at pH 4.5. After cooling to 5° C., the aqueous phase was acidified to pH 2.3 with 2 N HCl and the precipitate was filtered off. 1.13 g of the title compound could be isolated in this way.

NMR (DMSO-$d_6$): δ=9.5 ppm (d, 1H, CONH); δ=7.3 ppm (s, 2H, $NH_2$); δ=5.75 ppm (q, 1H, C-7-H); δ=5.05 ppm (d, 1H, C-6-H); δ=4.3 ppm (AB, 2H, $CH_2$-S); δ=3.8 ppm [230 Hz] (s, 3H, $OCH_3$, syn); δ=3.3 ppm (broad, C-2-$CH_2$); δ=2.65 ppm (s, 3H, $CH_3$).

EXAMPLE 5

7-[α-Syn-methoxyimino-α-(2-amino-5-chlorothiazol-4-yl)-acetamido]-3-(2-methyl-1,3,4-thiadiazol-5-yl-thiomethyl)-3-cephem-4-carboxylic acid 4.9 g of 7-[2-syn-methoxyimino-α-(2-amino-5-chlorothiazol-4-yl)-acetamido]-cephalosporanic acid and 1.5 g of 2-methyl-1,3,4-thiadiazole-5-thiol were dissolved in 70 ml of $H_2O$ at pH 6.5–7.0 by adding solid $NaHCO_3$. After the addition of 30 ml of acetone, the solution was stirred for 2½ hours at pH 6.5–7.0 and under reflux. The acetone was then stripped off on a rotary evaporator and the solution was acidified to pH 2.3 with 2 N HCl, at 5° C., while stirring. 2.7 g of the title compound, the physical constants of which were identical to those of the compound prepared in 4, could be isolated by filtration.

EXAMPLE 6

7-[α-Syn-methoxyimino-α-(2-amino-5-chlorothiazol-4-yl)-acetamido]-3-(2-amino-1,3,4-thiadiazol-5-yl-thiomethyl)-3-cephem-4-carboxylic acid If 2.5 g of 7-[α-syn-methoxyimino-α-(2-amino-5-chlorothiazol-4-yl)-acetamido]-cephalosporanic acid are reacted with 0.7 g of 2-amino-1,3,4-thiadiazole-5-thiol analogously to Example 5, 1.8 g of the title compound are obtained.

NMR (DMSO-$d_6$): δ=9.5 ppm (d, 1H, CONH); δ=7.0–7.5 ppm (broad signal, 4H, thiazole-$NH_2$ and thiadiazole-$NH_2$); δ=5.65 ppm (q, 1H, C-7-H); δ=5.0 ppm (d, 1H, C-6-H); δ=4.1 ppm (AB, $CH_2$S); δ=3.9 ppm [231 Hz] (s, 3H, $OCH_3$, syn!); δ=3.2 ppm (broad, C-2-$CH_2$).

EXAMPLE 7

7-[α-Methoxyimino-α-(2-amino-5-chlorothiazol-4-yl)-acetamido]-3-(3-methyl-1,2,4-thiadiazol-5-yl-thiomethyl)-3-cephem-4-carboxylic acid If 2.5 g of 7-[α-syn-methoxyimino-α-(2-amino-5-chlorothiazol-4-yl)-acetamido]-cephalosporanic acid are reacted with 0.75 g of 3-methyl-1,2,4-thiadiazole-5-thiol analogously to Example 5, 1.3 g of the title compound are obtained.

NMR (DMSO-$d_6$): δ=9.5 ppm (d, 1H, CONH); δ=7.45 ppm (s, broad, 2H, $NH_2$); δ=5.70 ppm ((q, 1H, C-7-H); δ=5.05 ppm (d, 1H, C-6-H); δ=4.15 ppm (AB, $CH_2$S); δ=3.95 ppm [232 Hz] (s, 3H, $OCH_3$, syn!); δ=3.1 ppm (broad, C-2-$CH_2$).

EXAMPLE 8

7-[α-Syn-methoxyimino-α-(2-amino-5-chloro-thiazol-4-yl)-acetamido]-3-[2-(thien-2-yl)-1-H-1,3,4-triazol-5-yl-thiomethyl]-3-cephem-4-carboxylic acid 2.35 g of α-syn-methoxyimino-α-(2-amino-5-chloro-thiazol-4-yl)-acetic acid were dissolved in 25 ml of tetrahydrofuran, 1.35 g of 1-hydroxybenzotriazole were added and the resulting mixture was warmed to 45°. After the addition of 2.16 g of dicyclohexylcarbodiimide, the mixture was stirred for 2 hours at room temperature and the urea which had precipitated out (1.9 g) was then filtered off. The filtrate was combined with a solution of 4.0 g of 7-amino-3-(2-thien-2-yl-1-H-1,3,4-triazol-2-yl-thiomethyl)-3-cephem-4-carboxylic acid and 3.0 g of triethylamine in 30 ml of $CH_2Cl_2$ and the resulting mixture was stirred for 8 hours at room temperature and then left in a refrigerator for 1 week. The solvent was removed in vacuo, the residue was taken up in 100 ml of $H_2O$ and the aqueous mixture was extracted three times with ethyl acetate at pH 4.5. The aqueous phase was then acidified to pH 2.0 with 2 N HCl, at 0°–5°. 400 mg of the title compound could be isolated in this way.

NMR (DMSO-$d_6$): $\delta=9.5$ ppm (d, 1H, CONH); $\delta=7.4$ ppm (broad, NH$_2$); $\delta=7.7$–7.5 ppm (m, 2H, thienyl); $\delta=7.5$–7.0 ppm (m, 2H, thienyl); $\delta=5.7$ ppm (q, 1H, C-7-H); $\delta=5.1$ ppm (d, 1H, C-6-H); $\delta=4.3$ ppm (broad, 2H, CH$_2$-S); $\delta=3.9$ ppm [232 Hz] (s, 3H, OCH$_3$, syn); $\delta=3.7$ ppm (broad, C-2-CH$_2$).

EXAMPLE 9

7-[α-Syn-methoxyimino-α-(2-amino-5-chlorothiazol-4-yl)-acetamido]-3-(5-carboxymethyl-4-methylthiazol-2-yl-thiomethyl)-3-cephem-4-carboxylic acid 940 mg of α-syn-methoxyimino-α-(2-amino-5-chloro-thiazol-4-yl)-acetic acid and 540 mg of 1-hydroxybenzotriazole were dissolved in 40 ml of tetrahydrofuran, and 824 mg of dicyclohexylcarbodiimide were added. After stirring for one hour, the solid was filtered off. A solution of 2.0 g of 7-amino-3-(5-carboxymethyl-4-methylthiazol-2-yl-thiomethyl)-3-cephem-4-carboxylic acid, dissolved in 30 ml of methylene chloride, 2.0 g of triethylamine, 2.0 ml of dimethylformamide and 0.3 ml of $H_2O$ was added to the mother liquor. The resulting mixture was stirred overnight at room temperature, the solvent was distilled off in vacuo, 50 ml of $H_2O$ were added and the aqueous mixture was extracted four times with ethyl acetate at pH 4.5. After cooling to $+5°$, the aqueous phase was acidified to pH 2.0 with 2 N HCl and the precipitate was collected by filtration: 1.26 g.

NMR (DMSO-$d_6$): $\delta=9.5$ ppm (d, 1H, CONH); $\delta=7.4$ ppm (s, broad, 2H, NH$_2$); $\delta=5.75$ ppm (q, 1H, C-7-H); $\delta=5.05$ ppm (d, 1H, C-6-H); $\delta=4.2$ ppm (AB, CH$_2$-S); $\delta=3.9$ ppm [230 Hz] (s, 3H, OCH$_3$, syn); $\delta=3.8$ ppm [224 Hz] (s, 2H, CH$_2$-CO$_2$H); $\delta=3.3$ ppm (broad, C-2-CH$_3$);

$\delta=2.2$ ppm (s, 3H, CH$_3$).

EXAMPLE 10

7-[α-Syn-methoxyimino-α-(2-amino-5-chlorothiazol-4-yl)-acetamido]-3-(2-trifluoromethyl-1,3,4-thiadiazol-5-yl-thiomethyl)-3-cephem-4-carboxylic acid If 2 g of 7-amino-3-(2-trifluoromethyl-1,3,4-thiadiazol-5-yl-thiomethyl)-3-cephem-4-carboxylic acid are reacted with the product resulting from the reaction of 1.18 g of α-syn-methoxyimino-α-(2-amino-5-chloro-thiazol-4-yl)-acetic acid, 680 mg of 1-hydroxybenzotriazole and 1.03 g of dicyclohexylcarbodiimide, analogously to Example 4, 1.7 g of the title compound are obtained.

NMR (DMSO-$d_6$): $\delta=9.5$ ppm (d, 1H, CONH); $\delta=7.2$ ppm (broad, 2H, NH$_2$); $\delta=5.65$ ppm (q, 1H, C-7-H); $\delta=5.0$ ppm (d, 1H, C-6-H); $\delta=4.3$ ppm (broad s, CH$_2$-S); $\delta=3.85$ ppm [231 Hz] (s, 3H, OCH$_3$, syn); $\delta=3.25$ ppm (broad, C-2-CH$_2$).

EXAMPLE 11

7-[α-Syn-methoxyimino-α-(2-amino-5-chlorothiazol-4-yl)-acetamido]-3-(2-trifluoromethyl-1,3,4-thiadiazol-5-yl-thiomethyl)-3-cephem-4-carboxylic acid 5.0 g of 7-[α-syn-methoxyimino-α-(2-amino-5-chloro-thiazol-4-yl)-acetamido]-cephalosporanic acid and 2.2 g of 2-trifluoromethyl-1,3,4-thiadiazole-5-thiol were dissolved in 70 ml of $H_2O$ at pH 6.5 by adding solid NaHCO$_3$. After the addition of 40 ml of ethyl acetate, the mixture was heated under reflux for 2 hours and cooled and the aqueous phase was separated. Residual ethyl acetate was removed from the aqueous phase on a rotary evaporator. The aqueous phase was acidified to pH 2.0 with 2 N HCl, at 5°, while stirring. 4.3 g of the title compound, the physical constants of which were identical to those of the compound prepared in Example 10, could be isolated by filtration.

EXAMPLE 12

7-[α-Syn-methoxyimino-α-(2-amino-5-chlorothiazol-4-yl)-acetamido]-3-(1,2-dimethyl-1,3,4-triazol-5-yl-thiomethyl)-3-cephem-4-carboxylic acid If 2.5 g of 7-[α-syn-methoxyimino-α-(2-amino-5-chlorothiazol-4-yl)-acetamido]-cephalosporanic acid are reacted with 0.7 g of 1,2-dimethyl-1,3,4-triazole-5-thiol analogously to Example 11, 2.25 g of the title compound are obtained.

NMR (DMSO-$d_6$): $\delta=9.5$ ppm (d, 1H, CONH); $\delta=7.15$ ppm (s, broad, 2H, NH$_2$); $\delta=5.70$ ppm (q, 1H, C-7-H); $\delta=5.05$ ppm (d, 1H, C-6-H); $\delta=4.1$ ppm (s, broad, CH$_2$-S); $\delta=3.85$ ppm [231 Hz] (s, 3H, OCH$_3$, syn); $\delta=3.6$ ppm (s, broadened, 3H, N-C$_3$+C-2-CH$_2$); $\delta=2.3$ ppm (s, 3H, CH$_3$).

EXAMPLE 13

7-[α-Syn-methoxyimino-α-(2-amino-5-chlorothiazol-4-yl)-acetamido]-3-(6-hydroxy-4-methyl-4,5-dihydro-1,2,4-triazin-5-on-3-yl-thiomethyl)-3-cephem-4-carboxylic acid If 2.5 g of 7-[α-syn-methoxyimino-α-(2-amino-5-chlorothiazol-4-yl)-acetamido]-cephalosporanic acid are reacted with 0.85 g of 6-hydroxy-4-methyl-3-mercapto-4,5-dihydro-1,2,4-triazin-5-one analogously to Example 11, 1.97 g of the title compound are obtained.

NMR (DMSO-$d_6$): $\delta=9.5$ ppm (d, 1H, CONH); $\delta=7.2$ ppm (s, broad, NH$_2$); $\delta=5.75$ ppm (q, 1H, C-7-H); $\delta=5.1$ ppm (d, 1H, C-6-H); $\delta=4.05$ ppm (s, broad, CH$_2$-S); $\delta=3.8$ ppm [230 Hz] (s, 3H, OCH$_3$, syn); $\delta=3.5$ ppm (s, broad, C-2-CH$_2$); $\delta=3.3$ ppm (s, 3H, N-CH$_3$).

EXAMPLE 14

7-[α-Syn-methoxyimino-α-(2-amino-5-chlorothiazol-4-yl)-acetamido]-3-(4,6-diaminopyrimidin-2-yl-thiomethyl)-3-cephem-4-carboxylic acid If 2.5 g of 7-[α-syn-methoxyimino-α-(2-amino-5-chlorothiazol-4-yl)-acetamido]-cephalosporanic acid are reacted with 0.8 g of 4,6-diaminopyrimidine-2-thiol analogously to Example 11, 1.5 g of the title compound are obtained.

NMR (DMSO-d$_6$): δ=9.5 ppm (d, 1H, CONH); δ=7.15 ppm (s, broad, NH$_2$); δ=5.75 ppm (q, 1H, C-7-H); δ=5.0–5.1 ppm (m, 2H, C-6-H+pyrimidine-H); δ=4.2 ppm (broad, CH$_2$-S) δ=3.85 ppm [231 Hz] (s, 3H, OCH$_3$, syn); δ=3.5 ppm (broad, C-2-CH$_2$).

EXAMPLE 15

7-[α-Syn-ethoxyimino-α-(2-amino-5-chlorothiazol-4-yl)-acetamido]-3-(1-methyltetrazol-5-yl-thiomethyl)-3-cephem-4-carboxylic acid If 990 mg of α-syn-ethoxyimino-α-(2-amino-5-chlorothiazol-4-yl)-acetic acid, 540 mg of 1-hydroxybenzotriazole and 830 mg of dicyclohexylcarbodiimide are reacted with 1.35 g of 7-amino-3-(1-methyltetrazol-5-yl-thiomethyl)-3-cephem-4-carboxylic acid analogously to Example 1, 0.95 g of the title compound is obtained.

NMR (DMSO-d$_6$): δ=9.5 ppm (d, 1H, CONH); δ=7.2 ppm (broad, 2H, NH$_2$); δ=5.7 ppm (q, 1H, C-7-H); δ=5.0 ppm (d, 1H, C-6-H); δ=4.15 ppm (q, 2H, OCH$_2$CH$_3$); δ=4.3 ppm (broad, CH$_2$-S); δ=4.0 ppm (s, 3H, tetrazole-CH$_3$); δ=3.6 ppm (s, broad, C-2-CH$_2$); δ=1.25 ppm (t, 3H, OCH$_2$CH$_3$).

EXAMPLE 16

7-[α-Syn-ethoxyimino-α-(2-amino-5-chlorothiazol-4-yl)-acetamido]-3-(2-methyl-1,3,4-thiadiazol-5-yl-thiomethyl)-3-cephem-4-carboxylic acid If 1.23 g of α-syn-ethoxyimino-α-(2-amino-5-chlorothiazol-4-yl)-acetic acid, 680 mg of 1-hydroxybenzotriazole and 1.03 g of dicyclohexylcarbodiimide are reacted with 1.72 g of 7-amino-3-(2-methyl-1,3,4-thiadiazol-2-yl-thiomethyl)-3-cephem-4-carboxylic acid analogously to Example 4, 2.15 g of the title compound are obtained.

NMR (DMSO-d$_6$): δ=9.5 ppm (d, 1H, CONH); δ=7.3 ppm (s, broad, NH$_2$); δ=5.75 ppm (q, 1H, C-7-H); δ=5.0 ppm (d, 1H, C-6-H); δ=4.1 ppm (q, 2H, OCH$_2$CH$_3$); δ=4.3 ppm (AB, 2H, CH$_2$-S); δ=3.2 ppm (broad, C-2-CH$_2$); δ=2.65 ppm (s, 3H, CH$_3$); δ=1.2 ppm (t, 3H, OCH$_2$CH$_3$).

EXAMPLE 17

7-[α-Syn-ethoxyimino-α-(2-amino-5-chlorothiazol-4-yl)-acetamido]-3-azidomethyl-3-cephem-4-carboxylic acid If 1.23 g of α-syn-ethoxyimino-α-(2-amino-5-chlorothiazol-4-yl)-acetic acid, 680 mg of 1-hydroxybenzotriazole and 1.03 g of dicyclohexylcarbodiimide are reacted with 1.25 g of 7-amino-3-azidomethyl-3-cephem-4-carboxylic acid analogously to Example 3, 1.9 g of the title compound are obtained.

NMR (DMSO-d$_6$): δ=9.5 ppm (d, 1H, CONH); δ=7.3 ppm (s, broad, NH$_2$); δ=5.65 ppm (q, 1H, C-7-H); δ=5.05 ppm (d, 1H, C-6-H); δ=4.15 ppm (q, 2H, OCH$_2$CH$_3$); δ=4.4 ppm (AB, CH$_2$-N$_3$); δ=3.4 ppm (broad, C-2-CH$_2$); δ=1.25 ppm (t, 3H, OCH$_2$CH$_3$).

EXAMPLE 18

7-[α-Syn-methoxyimino-α-(2-amino-5-chlorothiazol-4-yl)-acetamido]-3-(6-hydroxy-4-methyl-4,5-dihydro-1,2,4-triazin-5-on-3-yl-thiomethyl)-3-cephem-4-carboxylic acid 4.7 g of α-syn-methoxyimino-α-(2-amino-5-chlorothiazol-4-yl)-acetic acid are dissolved in 60 ml of tetrahydrofuran with the addition of 2.7 g of 1-hydroxybenzotriazole, and 4.12 g of dicyclohexylcarbodiimide are added. After stirring for one hour at room temperature, the solid is filtered off. The mother liquor is added to a solution of 7.4 g of 7-amino-3-(6-hydroxy-4-methyl-4,5-dihydro-1,2,4-triazin-5-on-3-yl-thiomethyl)-3-cephem-4-carboxylic acid and 2 g of triethylamine in 100 ml of tetrahydrofuran, 16 ml of dimethylformamide and 52 ml of H$_2$O. After stirring for 4½ hours at room temperature, the mixture was concentrated to about 50 ml on a rotary evaporator and the residue was cooled to 0° C. and adjusted to pH 4 with 2 N HCl. The resulting mixture was extracted with three 50 ml portions of ethyl acetate, the residual ethyl acetate was removed from the aqueous phase in vacuo and the aqueous phase was acidified to pH 2.0 with 2 N HCl. The precipitate formed was filtered off and dried. This yielded 3.7 g of the title compound, the physical constants of which were identical to those of the compound prepared in Example 13.

EXAMPLE 19

7-[α-Syn-methoxyimino-α-(2-amino-5-chlorothiazol-4-yl)-acetamido]-3-(6-hydroxy-4-ethyl-4,5-dihydro-1,2,4-triazin-5-on-3-yl-thiomethyl)-3-cephem-4-carboxylic acid If a procedure analogous to that of Example 18 is followed and 7.7 g of 7-amino-3-(6-hydroxy-4-ethyl-4,5-dihydro-1,2,4-triazin-5-on-3-yl-thiomethyl)-3-cephem-4-carboxylic acid are used, 3.2 g of the title compound are obtained.

NMR (DMSO-d$_6$): =12.4 ppm (s, OH); =9.5 ppm (d, 1H, CONH$_4$); =7.1 ppm (s, broad, NH$_2$); =5.75 ppm (q, 1H, C-7-H); =5.1 ppm (d, 1H, C-6-H); =4.05 ppm (broad, CH$_2$S); =3.8 ppm [230 Hz] (s, 3H, OCH$_3$, syn); =1.2 ppm (t, 3H, CH$_2$CH$_3$).

EXAMPLE 20

7-[α-Syn-methoxyimino-α-(2-amino-5-chlorothiazol-4-yl)-acetamido]-3-(6-hydroxy-2-methyl-2,5-dihydro-1,2,4-triazin-5-on-3-yl-thiomethyl)-3-cephem-4-carboxylic acid If a procedure analogous to that of Example 18 is followed and 7.4 g of 7-amino-3-(6-hydroxy-2-methyl-2,5-dihydro-1,2,4-triazin-5-on-3-yl-thiomethyl)-3-cephem-4-carboxylic acid are used, 2.53 g of the title compound are obtained.

NMR (DMSO-d$_6$): =9.5 ppm (d, 1H, CONH); =7.1 ppm (s, broad, NH$_2$); =5.75 ppm (dd, 1H, C-7-H); =5.1 ppm (d, 1H, C-6-H); =4.2 ppm (AB, CH$_2$S); =3.8 ppm [231 Hz] (s, 3H, OCH$_3$, syn); =3.55 ppm (s, 3H, N-CH$_3$).

We claim:

1. A compound of the formula

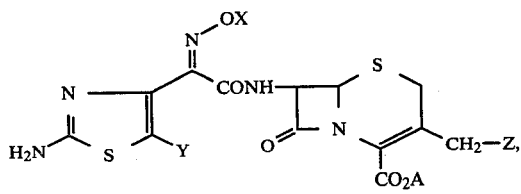

wherein
- X is hydrogen, (C₁–C₄) alkyl, or such alkyl substituted by halogen, hydroxy, amino, mono-(C₁–C₄)alkylamino, or di-(C₁–C₄)alkylamino, or wherein X is carboxymethyl, alkylcarbonylmethyl, aminocarbonylmethyl, cyanomethyl, or such carboxymethyl, alkylcarbonylmethyl, aminocarbonylmethyl, or cyanomethyl monosubstituted in the methylene group by (C₁–C₄) alkyl, disubstituted in the methylene group by (C₁–C₄)alkyl, or disubstituted in the methylene group by alkylene forming a 3- to 6-membered carbocyclic ring together with the methylene carbon, or wherein X is a carboxylate salt of carboxymethyl and a physiologically acceptable cation;
- Y is halogen;
- Z is -S-Het wherein Het is a five- or six-membered heterocyclic ring containing one nitrogen atom, such a ring containing at least one further hetero atom selected from the group consisting of nitrogen, oxygen, and sulfur, or such a ring containing one nitrogen atom or such a ring containing one nitrogen atom and at least one further hetero atom which ring is mono- or disubstituted by (C₁–C₄)alkyl, trifluoromethyl, carboxyl, carboxymethyl, (C₁–C₄)alkoxy-carbonylmethyl, hydroxy, hydroxymethyl, oxo, amino, mono-(C₁–C₄)alkylamino, di(C₁–C₄)alkylamino, (C₁–C₄)alkanoylamino, thienyl, or pyridyl; and
- A is hydrogen, a protected ester group for carboxyl, or a physiologically acceptable cation.

2. A pharmaceutical preparation for the treatment of microbial infections, comprising an antimicrobially effective amount of a compound as in claim 1 and a pharmaceutically acceptable carrier therefor.

3. The method of treating a microbial infection in a patient suffering therefrom which comprises orally or parenterally administering to said patient an antimicrobially effective amount of a compound as in claim 1.

4. A compound as in claim 1 which is

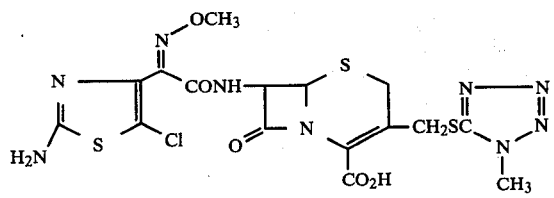

* * * * *